(12) United States Patent
Major (10) Patent No.: US 9,204,870 B2
(45) Date of Patent: Dec. 8, 2015

(54) DEVICE AND METHOD FOR THE POSITIONING OF TISSUE DURING LAPAROSCOPIC OR ENDOSCOPIC SURGERY

(71) Applicant: C Paul Major, LaGrange, GA (US)

(72) Inventor: C Paul Major, LaGrange, GA (US)

(73) Assignee: Tracey Stribling, La Grange, GA (US)

( * ) Notice: Subject to any disclaimer, the term of this patent is extended or adjusted under 35 U.S.C. 154(b) by 311 days.

(21) Appl. No.: 13/959,952

(22) Filed: Aug. 6, 2013

(65) Prior Publication Data

US 2013/0317307 A1 Nov. 28, 2013

Related U.S. Application Data

(63) Continuation of application No. 12/804,685, filed on Jul. 26, 2010, now abandoned.

(51) Int. Cl.
*A61B 17/00* (2006.01)
*A61B 17/02* (2006.01)
*A61B 17/29* (2006.01)

(52) U.S. Cl.
CPC ............ *A61B 17/0218* (2013.01); *A61B 17/29* (2013.01); *A61B 2017/00464* (2013.01); *A61B 2017/294* (2013.01); *A61B 2017/2931* (2013.01)

(58) Field of Classification Search
CPC ........... A61B 17/0218; A61B 17/0466; A61B 17/0482; A61B 17/0483; A61B 17/0487; A61B 17/0491; A61B 17/06061; A61B 17/062; A61B 17/083; A61B 17/122; A61B 17/1222; A61B 17/128; A61B 17/1285; A61B 17/22; A61B 17/22031; A61B 2017/00349; A61B 2017/00464; A61B 2017/00473; A61B 2017/047; A61B 2017/081; A61B 2017/22034; A61B 2017/22035; A61B 2017/22041; A61B 2017/22045; A61B 2017/249; A61B 2017/2931; A61B 2017/294
USPC .................................................. 606/205–207
See application file for complete search history.

(56) References Cited

U.S. PATENT DOCUMENTS

| | | | | |
|---|---|---|---|---|
| 5,242,456 | A * | 9/1993 | Nash et al. | 606/142 |
| 5,415,666 | A * | 5/1995 | Gourlay et al. | 606/142 |
| 8,377,044 | B2 * | 2/2013 | Coe et al. | 606/1 |
| 2003/0010659 | A1 * | 1/2003 | Hernandez | 206/366 |
| 2008/0200751 | A1 * | 8/2008 | Browning | 600/30 |
| 2010/0249498 | A1 * | 9/2010 | Wingardner et al. | 600/104 |

* cited by examiner

*Primary Examiner* — David C Eastwood
*Assistant Examiner* — Martin T Ton
(74) *Attorney, Agent, or Firm* — J.T. Hollin, Attorney at Law, P.C.

(57) ABSTRACT

A surgical device and method for the retracting, maneuvering, and re-positioning of tissue and/or a body organ during endoscopic and laparoscopic procedures. The surgical apparatus comprises at least one separable grasping device with a detachable head, and an exteriorly-operated handle mechanism, or puppet handle. The disclosed device enables a physician, using a plurality of lengths of sutures simultaneously connected to (a) stems of the exteriorly exposed puppet handle and (b) the detachable head, positioned at clasping points on the organ, to rearrange the orientation of tissue or the organ for better accessibility, analysis, and/or exposure to accompanying surgical instruments in situ. The method presented minimizes the number of bodily incisions required to perform surgery by means of endoscope or laparoscopic equipment.

4 Claims, 10 Drawing Sheets

DEVICE AND METHOD FOR THE POSITIONING OF TISSUE DURING LAPAROSCOPIC OR ENDOSCOPIC SURGERY

CROSS-REFERENCES TO RELATED APPLICATIONS

This is a Continuation application which claims the benefit of priority from U.S. non-provisional application Ser. No. 12/804,685, filed on Jul. 26, 2010, and said non-provisional application being incorporated herein by reference. This application further claims priority from U.S. Provisional Application, Ser. No. 61/271,842, filed on Jul. 27, 2009, said provisional application being incorporated herein by reference.

FEDERALLY-SPONSORED RESEARCH & DEVELOPMENT

There is no federally sponsored research or development in connection with this inventive concept.

NAMES OF THE PARTIES TO A JOINT RESEARCH AGREEMENT

There is no joint research agreement applicable to this inventive concept.

BACKGROUND OF THE INVENTION (1) Field of the Invention

The present inventive concept, among other uses and applications, primarily relates to an improved surgical instrument and a method which will enable a physician to perform laparoscopic or endoscopic surgery with a minimum amount of bodily incisions to a patient's body. The device under consideration is an improvement on what is known in the medical profession as a grasper.

Graspers come in a wide of variety of functional designs, which are intended for specific purposes. Various types of graspers include tissue, claw, sharp tooth, endo-clinch, alligator, aggressive, cobra tooth, spoon, cup, babcock, DeBakey, and Allis graspers.

(2) Description of the Related Art

Graspers are used to clasp bodily tissue or an internal organ and, often to reposition the tissue or organ for better utilization of other instruments which may be required during a laparoscopic surgical process. The grasper is typically inserted into the abdominal cavity by means of insertion through the inner channel of a trocar, said trocar having been initially used to pierce the abdominal wall in the vicinity of the subject organ or tissue. Usually, a second trocar is also required as a means of inserting other surgical instruments to perform operations on the organ or tissue being held by the grasper.

Over the years, various surgical instruments and complex trocar designs have been devised to perform separate multiple functions during laparoscopic surgery. A recent patent, U.S. Pat. No. 7,318,802 (Suzuki, 2008), discloses a combination of an endoscope and a grasping, device which, when used together, are suited for operationally treating gastro esophageal reflux disease. The grasping device is specially designed for holding tissue formed at the junction the stomach and esophagus.

U.S. patent application publication #2005/0149066 (Stafford, 2005) presents a device for laparoscopally suturing tissue, comprising an elongated shall which, upon being inserted through the abdominal wall, deploys two mechanical arms, each arm having a means of receiving a needle and its respective suture.

U.S. patent application publication #2009/0062816 (Weber, 2009), discloses an apparatus comprising a manually operated handle attached to the proximal end of a lengthy shaft. The handle further comprises two separate mechanical operating devices, one being attached to a pair of grasping jaws at the distal end of the shaft and the other device serving to advance suture to two needles, also at the distal end of the shaft. The handle may mechanically advance the suture.

U.S. patent application publication #2007/0123914 (Lizardi et al, 2007) presents a needle passer instrument which has a needle engaging cartridge in the upper jaw and a surgical needle with attached suture mounted in the lower jaw. A needle actuation rod engages the surgical needle and pushes the needle through tissue contained between the jaws of the device.

BRIEF SUMMARY OF THE INVENTION

The present inventive concept, among other uses and applications, relates to an apparatus and method by which a physician may perform laparoscopic or endoscopic surgery within the abdominal cavity of a patient. The device gives the physician/surgeon a unique capability to reposition a body organ or tissue during the surgical procedure. An important object of the disclosed apparatus and method is to minimize the number of incisions and/or trocar placements into the abdominal wall during the course of a surgical procedure, while providing enhanced tissue positioning and retraction capability to the physician.

The primary components of the apparatus include a detachable grasping device comprising a detachable head, a grasper handle removably fixed to the detachable head, at least two needles on suture, which needles may be removably attached to the detachable head, and a storage handle, referred to as a "puppet handle," said handle maintained exteriorly to the abdominal wall. The detachable head may be separated from the grasper handle either exteriorly to the patient or after insertion into a patient proximate the actual operation situs.

Initiation of the surgical process is begun with the placement of a trocar through the abdominal wall of the patient. The grasping device is inserted through the channel of the trocar and positioned proximate the organ or tissue to be operated upon. For illustrative and ease of reference purposes only, the object of the surgical manipulations may be interchangeably referred to as "organ" or "tissue." Once the tissue is grasped by the detachable head of the grasping device, the grasper handle is removed from the detachable head. A secondary grasper is then inserted through the trocar for the purpose of removing the first of the two needles on suture from its retention means on the detachable head. The respective suture remains within its retention mechanism on the detachable head. The secondary grasper is then manipulated to a desired location or exit point on the interior of the abdominal wall, at which exit point the first needle and suture is impelled outwardly through the abdominal wall.

The foregoing procedure is repeated with the second needle and suture. Once outside the abdominal wall, the two needles and sutures are inserted into opposite ends of the puppet handle. The storage handle then becomes the means by which the operator may retract or reposition the organ as required for better vision and assessment during the surgical procedure. The puppet/storage handle may move either of the two stored needles/sutures, thereby directly re-positioning the organ at the point where the detachable head is grasping the tissue.

The reader is advised that, for the sake of convenience and clarity, the operation of this device has been described primarily with respect to the human body. However, the inventive concept is also suitable for use by veterinarians and other professionals where anatomical procedures internal to a vertebrate body are necessary. Therefore, the descriptions rendered herein are not considered to be restrictive or limiting of the operation of the device.

BRIEF DESCRIPTION OF THE VIEWS OF THE DRAWINGS

A more thorough understanding of the present invention and fabrication system may be had by reference to the drawings herein, of which a brief summation of each drawing follows.

Numerical Index to Nomenclature of Invention

| | |
|---|---|
| 1. | Separable grasping device |
| 2. | Grasping handle |
| 3. | (a) Grasping handle proximal end |
| | (b) Grasping handle distal end |
| 4. | Endoscope |
| 5. | Detachable head |

Numerical Index to Nomenclature of Invention

| | |
|---|---|
| | (a) Second detachable head |
| 6. | Upper jaw |
| 7. | Lower jaw |
| 8. | Jaws locking means |
| | (a) Jaws locking mechanism |
| | (b) Locking rod control |
| 9. | Head detaching means |
| | 9(a) Head detaching mechanism |
| 10. | Upper jaw motion linkage |
| 11. | Lower jaw motion linkage |
| 12. | Needle one fastening means |
| 13. | Needle two fastening means |
| 14. | Needle one |
| 15. | Needle two |
| 16. | Suture one |
| 17. | Suture two |
| 18. | Suture one harnessing means |
| 19. | Suture two harnessing means |
| 20. | Dual puppet handle |
| | (a) Left handle stem |
| | (b) Right handle stem |
| | (c) Extra handle stem |
| 21. | Triple-stem puppet handle |
| 22. | Multiple-stemmed puppet handle |
| 23. | Puppet handle connector means |
| 24. | Exit point one |
| 25. | Exit point two |
| | (a) Exit point three |
| 26. | Secondary grasping device |
| 27. | Inner abdominal wall |
| 28. | Outer abdominal wall |
| 29. | Body organ |
| 30. | n/a |
| 31. | Needle three |
| 32. | Needle four |
| 33. | Third Suture |
| 34. | Fourth Suture |
| 35. | Working port |
| 36. | Needle driver |
| 37. | Compressible material |
| 38. | Universal grasper device |
| 39. | Release mechanism |
| 40. | Needle one retainer |
| 41. | Needle two retainer |
| 42. | Pins: a), b), c), d) |
| 41.-49, | n/a |
| 50. | Square drive shaft (hollow) |
| 51. | Driven shaft (square) |
| 52. | Sleeve |
| 53. | Circumferential groove |
| 54. | Spring-loaded ball |
| 55. | U-joint |
| 56. | Locking ring |
| 57. | Control wheel |
| 58. | Gripping handle |
| 59. | Grasper head housing |
| 60. | Housing for detachable head |
| | (a) Stator |
| 61. | Threaded receptor |
| 61 | (a) Spring-loaded ball |
| | (b) Recessed seat |
| 62. | n/a |
| 63. | Clutch |
| 63. | (b) Clutch housing |
| 64. | Threaded locking rod |
| 65. | Handle shaft |

DETAILED DESCRIPTION OF THE INVENTION

Figure 1:
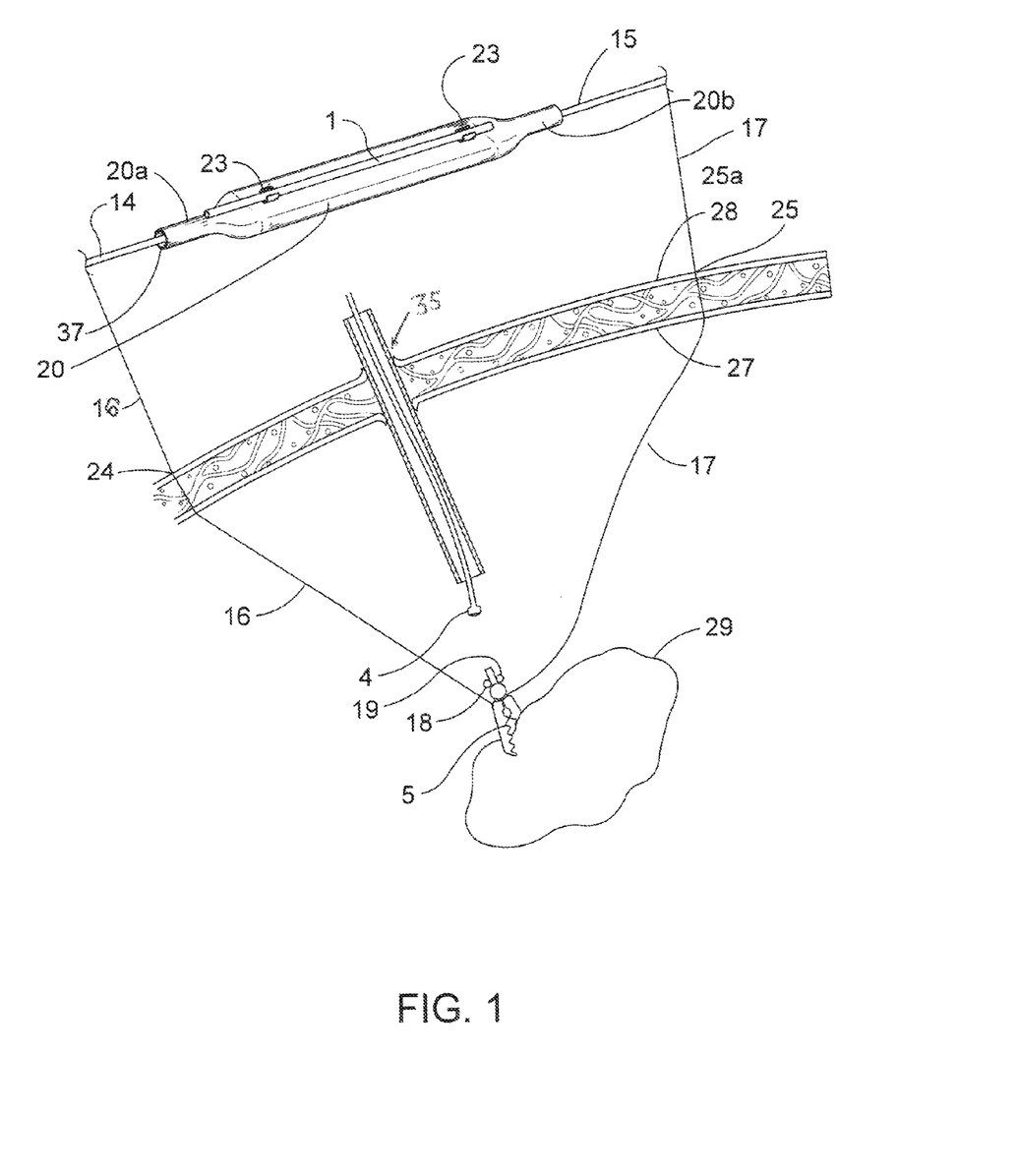
FIG. 1 is an overall view of the general positioning, functions, and maneuvering methods utilized with the basic inventive concept.

The description of this inventive concept will begin with reference to FIG. 1, where it can be seen that the general objective of the inventive concept is to attach the distal ends of suture one 16 and suture two 17 to the surgical object, which for illustrative and descriptive purposes only, will be assumed to be a body organ 29, by means of a detachable grasper head 5. The proximal ends of the sutures 16, 17, having been attached to needles 14, 15, are removed from the abdominal cavity by piercing, from inside to outside, the abdominal wall 28. For the sake of convenience and easy reference, said needles 14 and 15 shall be referred to as Keith needles, although any other surgical needle suitable for the purposes herein may also function in this inventive concept.

Figure 7:
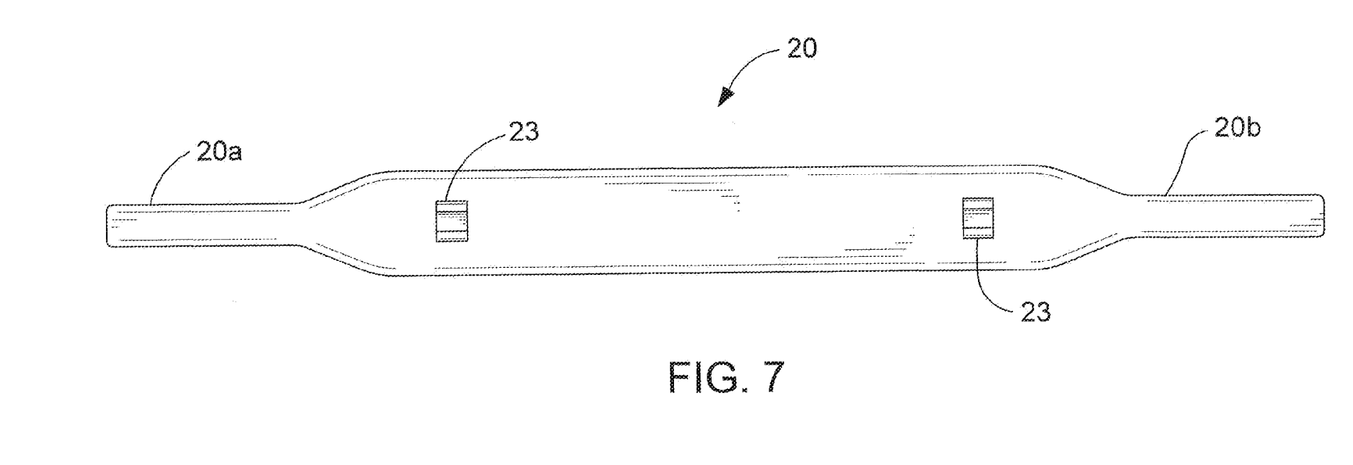
FIG. 7 is a plan view illustration of an embodiment of a dual puppet handle, as seen from the perspective of the physician holding the instrument.
Figure 7A:
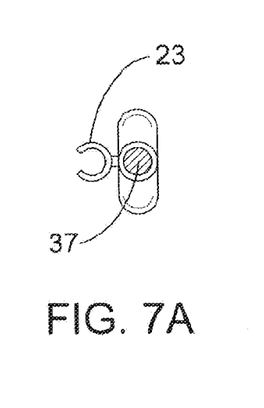
FIG. 7A is a left (or right) side end view of the dual puppet handle, of FIG. 7, above.
Figure 8:
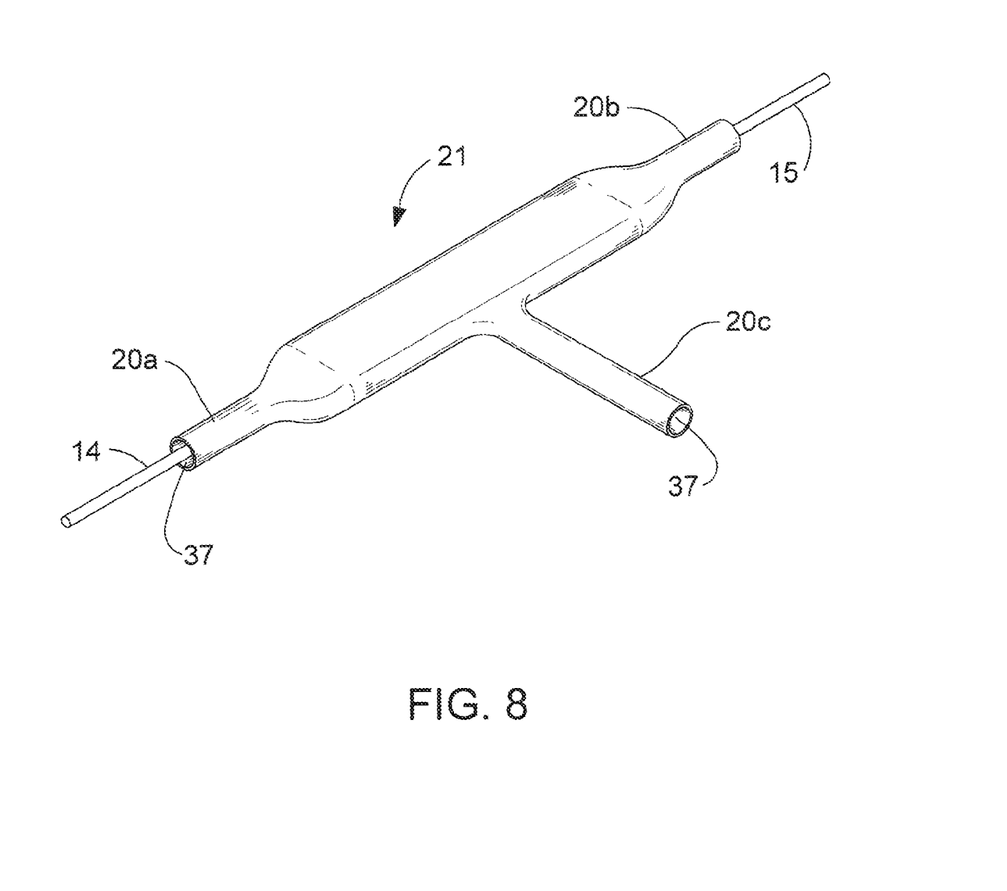
FIG. 8 illustrates a triple-stem puppet handle.
Figure 9:
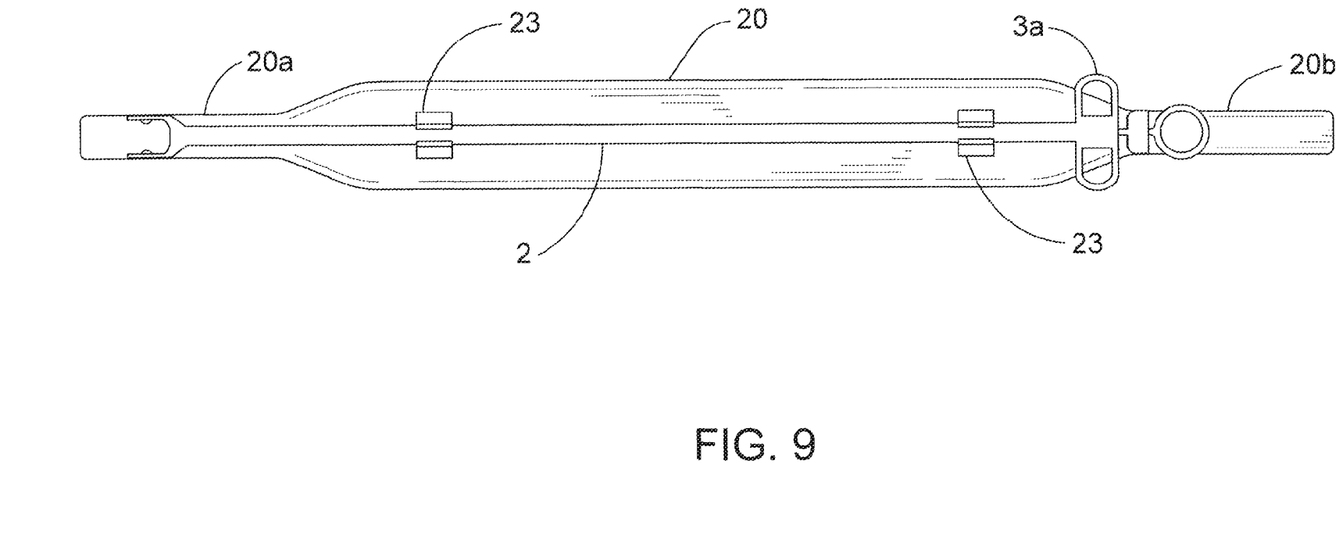
FIG. 9 depicts the stowage of a separable grasper handle onto the upper surface of a dual puppet handle.

Exterior to the patient's body, the Keith needles 14, 15 are then inserted into the respective stems 20a, 20b or ends of a dual- or multiple-tube storage handle, referred to as a "puppet handle" 20. The stems 20a, 20b of the puppet handles presented may be constructed with a variety of means for retention of the abdominally exiting needles, 14, 15. As shown in FIGS. 7 and 7A, the preferred embodiment comprises a compressible material 37 firmly compacted into the interior of each stem 20a, 20b to securely retain the needles 14, 15 after exiting the abdominal cavity 28 The dual puppet handle 20 may then be manipulated by the physician, at a variety of gentle pulling angles, to retract or reposition the body organ 29. An elementary puppet handle 20 is illustrated in FIG. 1, FIG. 7, and FIG. 9. A multiple-stem puppet handle 21 is shown in FIG. 8.

Any surgical procedure requiring piercing of a patient's abdominal cavity may be initiated by the placement of an initial trocar device through the outer and inner abdominal walls 28, 27, respectively. The penetration point of the initial trocar becomes the working port 35 for the surgery. Utilizing the initial trocar, an endoscope 4 may be inserted into the channel of the trocar or through the working port 35 created by the initial trocar. The endoscope 4 is then maneuvered to position the instrument proximate the body organ 29 which is the subject of the surgical procedure. The trocar may need to be gradually pressed to a greater depth, since immediately afterwards, the separable grasping device 1 is inserted, parallel to the tube of the endoscope 4, through the channel of the initial trocar or through the working port 35.

Figure 6:
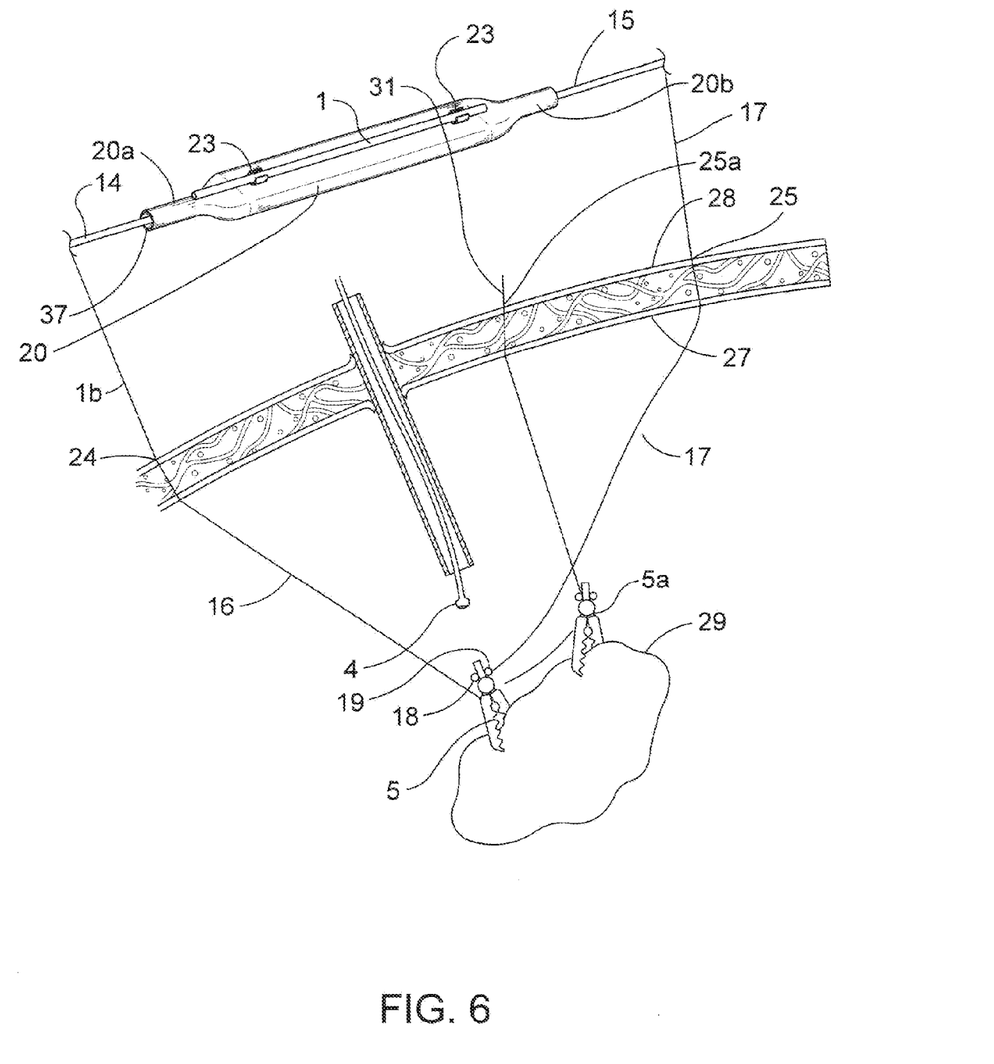
FIG. 6 depicts the method of positioning of two detachable heads onto a bodily organ during a surgical procedure.

By turning the attention to FIG. 6, it is observed that greater capability for surgical adaptation is provided, with the insertion of a second detachable head 5a attached to a different location on the body organ 29. Thus, the physician may make more accurate, or differently-oriented, placements of the body organ 29 for better access. The second detachable head 5a may be manipulated via its own third suture 33, which will likely be affixed to a third stem of the puppet handle 21 (as depicted in FIG. 8). Either or both the primary detachable head 5 or the second detachable head 5a may be constructed with wing clamps so as to remove the detachable heads 5, 5a, as necessary.

Figure 2:
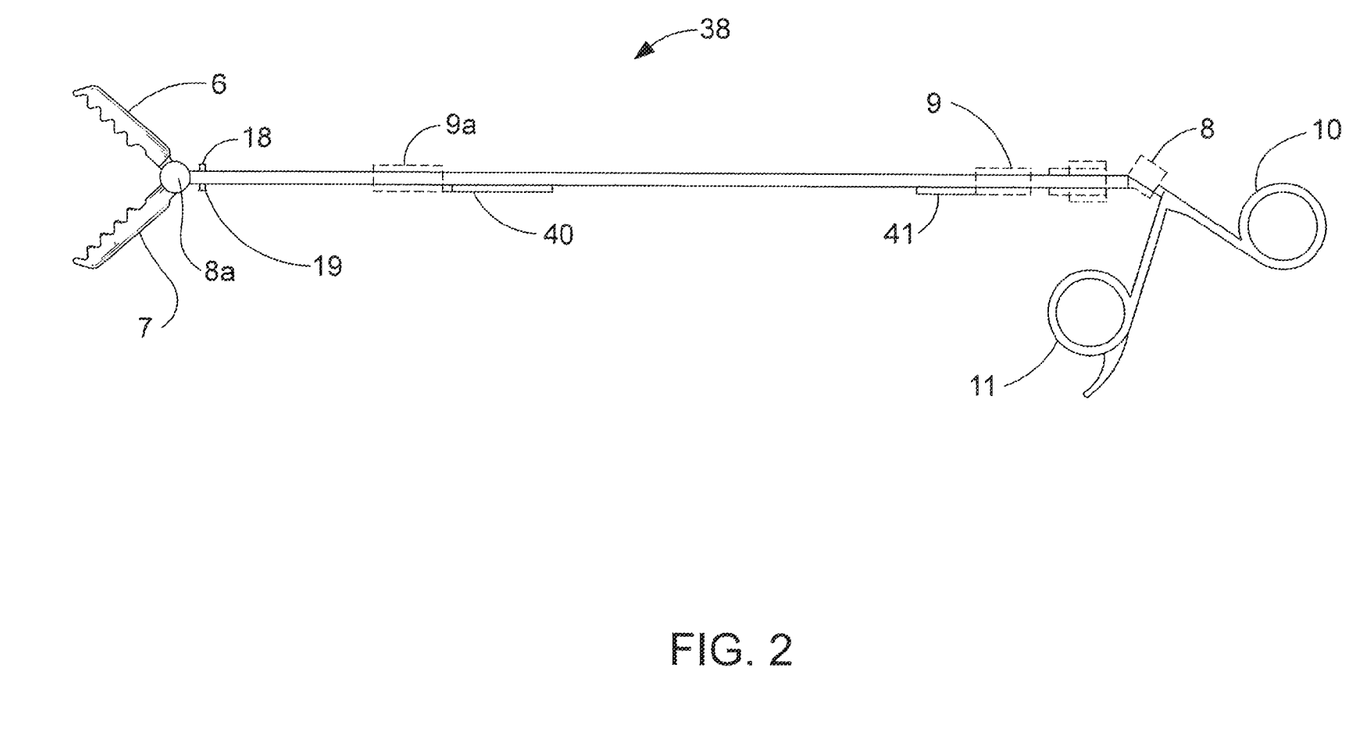
FIG. 2 depicts a stylized concept of a universal grasper device with a detachable head, the device also referred to as a separable grasping device

FIG. 2 depicts a general drawing of a generic universal grasper device 38 which is typical of embodiments of the inventive concept. The device may operate by several differing combinations of means for, and methods of connection. Once the device 38 is inserted through the initial trocar, the grasper's upper jaw 6 and lower jaw 7 are placed at the desired site on the subject tissue or body organ 29. The jaws 6, 7 must comprise non-traumatic teeth or Babcock type heads. Upper jaw 6 and lower jaw 7 motion control means 10, 11 are then operated through a connective means to gently close the grasper's upper jaw 6 and lower jaw 7 at the selected location. A jaws locking means 8 may be operated, through a jaws locking mechanism 8a, to securely attach the grasper head 5 to the body organ 29. The jaws locking means 8 may be an industry-common slide lock ratchet system, a rotary-type mechanism, or other means of securing the jaws 6, 7 of the grasper in a locked position.

Generally, the detachable grasper head 5 can be separated from its grasping handle 2 by a head detaching mechanism 9a which transmits control inputs through linkage to a head detaching means 9. At the time of separation, the needle one retainer 40 and needle two retainer 41 are also activated so as to release needle one 14 and needle two 15. Suture-harnessing means 18, 19 hold the respective sutures for needle one 14 and needle two 15. The suture-harnessing means 18, 19 may be small eyelets or hook-type retainers with inner diameters somewhat larger than the gauge of suture utilized. The two needles remain close to the grasper head 5 for the ensuing capture by a needle driver which is used to execute a piercing-type exit of each needle 14, 15 and its respective suture through the abdominal wall 28.

Figure 3:
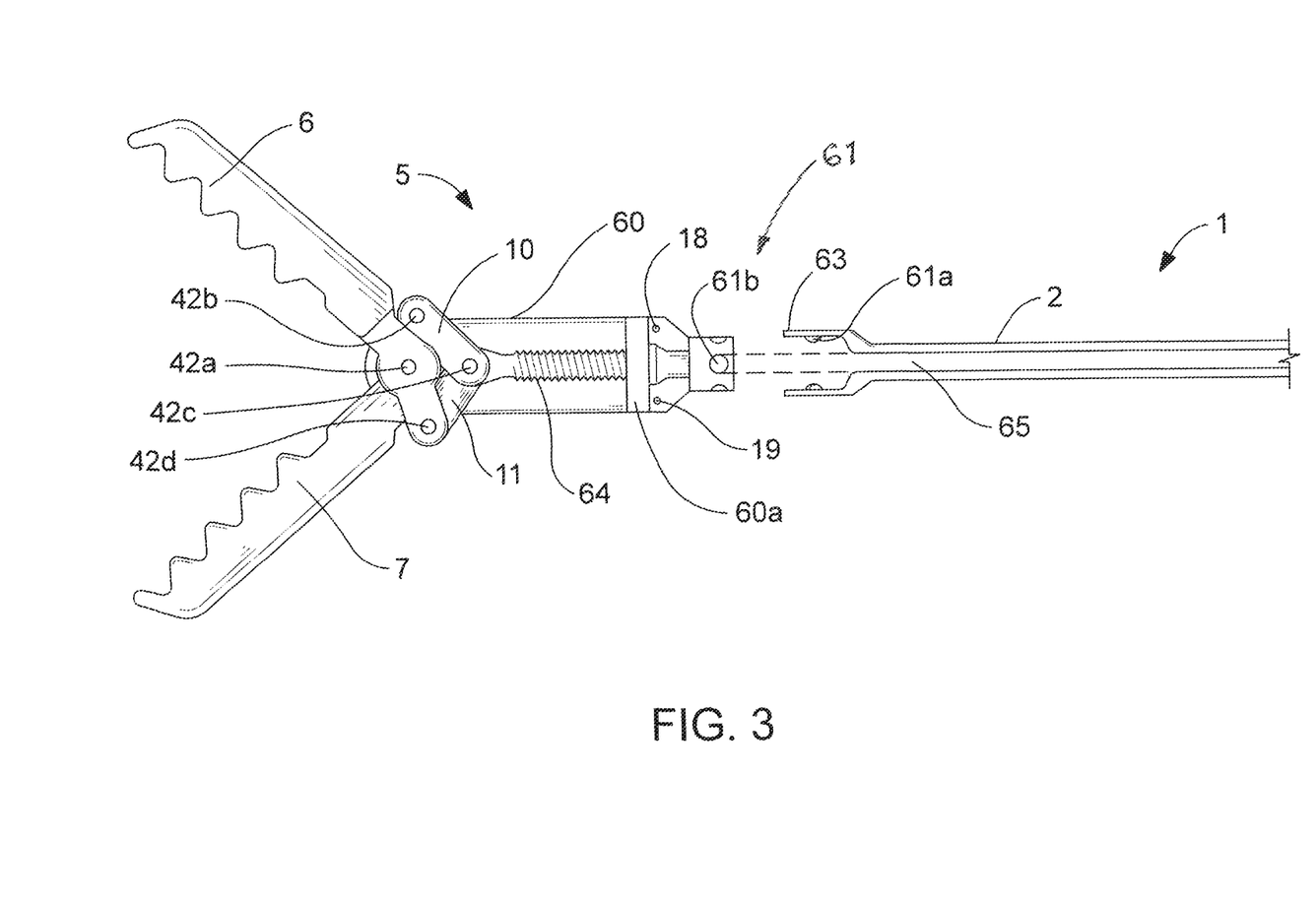
FIG. 3 illustrates a partial cutaway view of an embodiment of the distal end of a separable grasping device and the detachable grasper head.
Figure 3A:
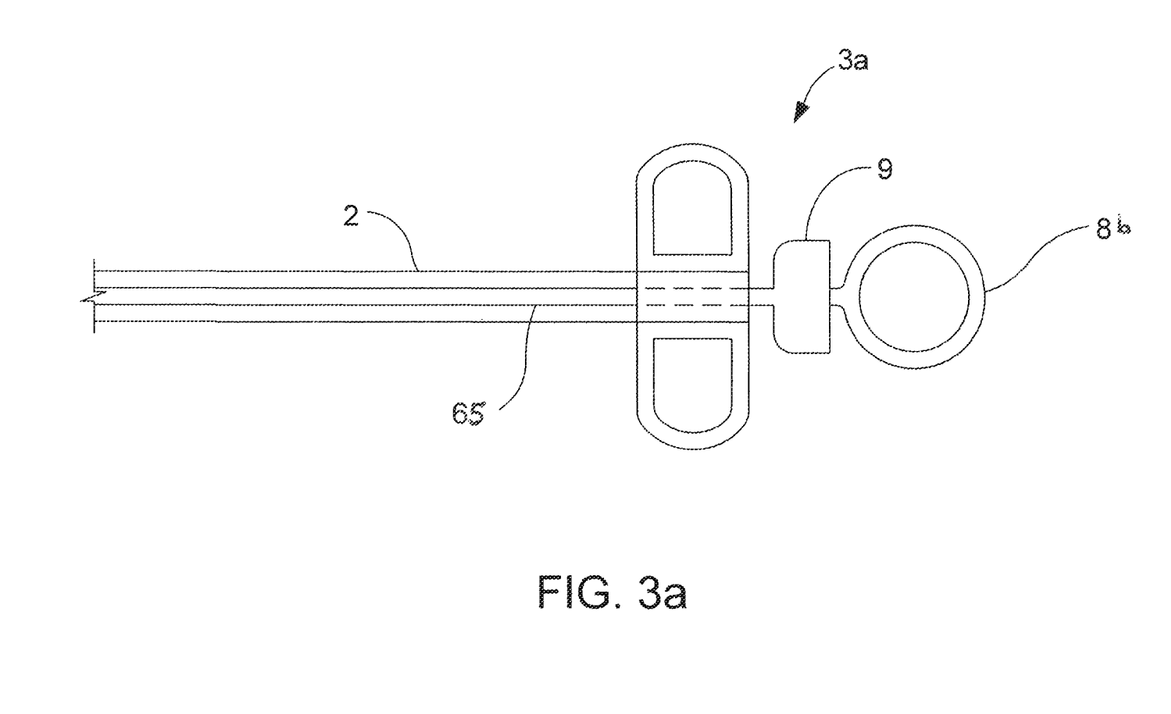
FIG. 3a depicts the proximal end of a separable grasping device, its grasper head detaching means, and its jaws locking means.
Figure 4:
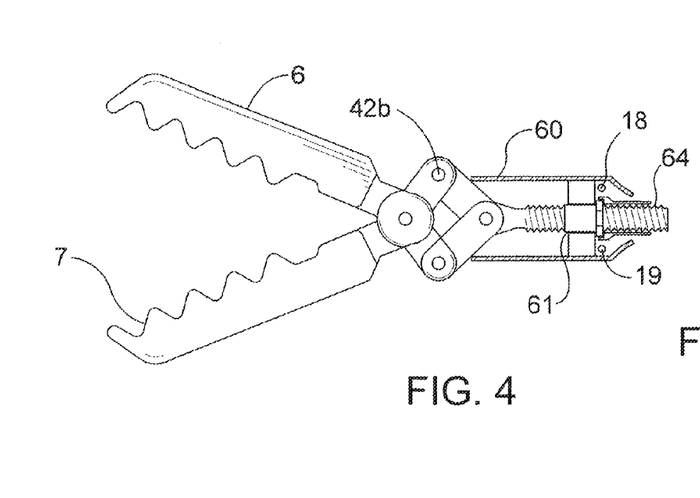
FIG. 4 presents the open position of the grasper jaws of an embodiment of the detachable head.
Figures 4A, 4B:
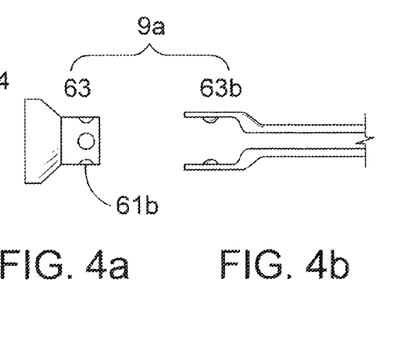
FIG. 4a and FIG. 4b combined illustrate the clutch and clutch housing of a particular embodiment of detaching means of a separable grasping device.
Figure 4C:
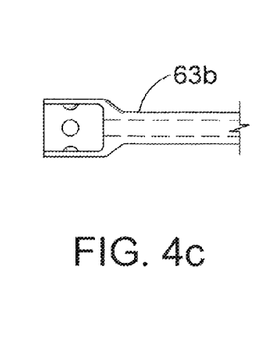
FIG. 4c depicts the union of the clutch and clutch housing of an embodiment of the separable grasping device.
Figure 5:
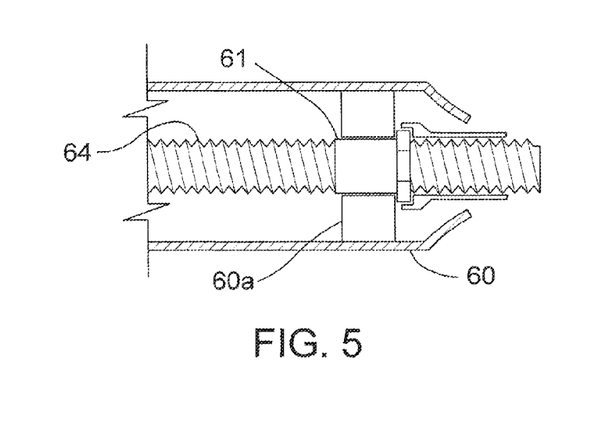
FIG. 5 illustrates a cutaway view of the threaded locking rod, which enables operation of the jaws of an embodiment of a detachable grasper head.
Figure 5A:
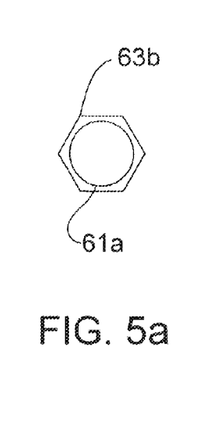
FIG. 5a presents an end view looking interiorly at the clutch of an embodiment of the separable grasping device.
Figure 5B:
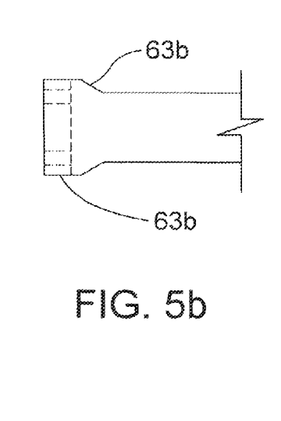
FIG. 5b presents a view of the clutch housing.

In turning the attention to a different embodiment, FIG. 3 and FIG. 3a show a separable grasping device 1 which is observed to be a combination of a grasping handle 2, disconnected from its detachable grasper head 5. The detachable grasper head 5 further comprises an upper jaw 6, lower jaw 7, an upper jaw motion linkage 10, a lower jaw motion linkage 11, a threaded receptor 61, and a head detaching means 9. In viewing FIGS. 3 and 3a, another embodiment of the inventive concept depicts a jaws locking means accomplished by a threaded locking rod 64, handle shaft 65, a locking, rod control 8b, and two suture harnessing means 18, 19. Provisions may also be made for needle retention mechanisms proximate, or on, the detachable grasper head 5.

At the proximal end of the separable grasping device 1, as shown in FIG. 3, the upper and lower jaw motion control linkages 10, 11 are operated by the threaded locking rod 64 so as to open the upper and lower jaws 6, 7 of the detachable head 5. While viewing the operational site through a laparoscope 4, the upper and lower jaws 6, 7, being in the closed position, are maneuvered into a desired location adjacent to a body organ 29. The jaws are thereupon opened and then closed upon the organ 29. Appropriately placed pins 42a-d, connecting the threaded locking rod 64 and the upper and lower jaw motion linkages 10 and 11 effectuate the opening and closing of both jaws 6, 7.

A dual-component threaded receptor 61 consisting of a clutch 63 having internally-embedded spring-loaded balls 61a, is integral to the grasping handle 2. The threaded receptor 61 further comprises a coaxial fitting having recessed seats 61b corresponding to the circumference of the spring-loaded bails 61a. A handle shaft 65 culminates in a threaded locking rod 64. The threads of the locking rod 64 engage compatible threads on the interior surface of a stator 60a. The stator 60a is permanently affixed to a detachable head housing 60.

The threaded receptor 61, comprising a spring-loaded ball 61(a) and a recessed seat 61(b), prevents further movement of the threaded locking rod 64 at certain rotated extensions of the locking rod control 8b and the handle shaft 65, thereby locking the jaws 6, 7 and securely maintaining the body organ 29 within the grasp of the detachable head 5. If necessary, a second separable grasping device 1(a) may be inserted into the initial trocar with another detachable grasper head 5(a), as shown in FIG. 6, and a separate length of a third suture 33 for additional retraction capability.

Referring to FIG. 3a, at the grasping handle proximal end the head detaching means 9 is activated to disengage the spring-loaded balls 61(a) from their respective recessed seats 61(b), thereby separating the detachable head 5 from the grasping handle 2. The grasping handle 2 is then removed from the initial trocar and placed in temporary storage within the puppet handle 20 connector means 23. Suture one 16 and suture two 17, being previously attached to needle one 14 and needle two 15, are now prepared for being drawn through suture one harnessing means 18 and suture two harnessing means 19, respectively. To accomplish this, a specialized grasper or needle driver 36 is inserted into the channel of the initial trocar and maneuvered into position to grasp each needle 14, 15, in sequence. Each needle is then positioned upward toward desired respective abdominal exit point one 24 and exit point two 25, as illustrated in FIG. 1.

Again referring to FIG. 1, at the exterior of each exit point 24 and 25, each of the two surgical needles 14, 15, along with their respective sutures 16, 17, are pulled through the outer abdominal wall 28. The needles 14, 15 are then firmly pushed into the compressible material 37 compacted into the respective stems 20(*a*), (*b*) of the dual puppet handle 20. After completion of extraction of the needles, the needle driver 36 is then withdrawn upwards through the initial trocar and properly stored. At this point, the operator may place other surgical instruments into the immediate vicinity of the body organ 29. The respective exteriorly-exposed sutures 16, 17 are secured at the dual puppet handle 20 so as to enable a physician, with reference to the endoscope 4 previously inserted, to position and/or retract the body organ 29 as necessary, by well-planned incremental movements of the puppet handle 20.

FIG. 9 demonstrates the manner in which the handle 2 of the separable grasping device 1 is attached for storage to the upper surface of a dual puppet handle 20 while the associated detachable head 5 is in use during the surgical procedure.

Figure 10A:
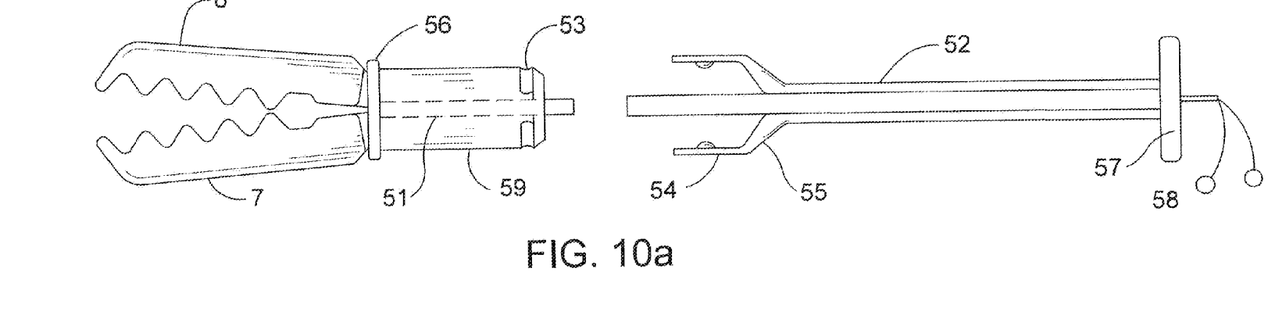
FIGS. 10a through 10c present a different embodiment of the separable grasper device wherein the internal operating mechanism is two interconnecting drive shafts.
Figure 10B:
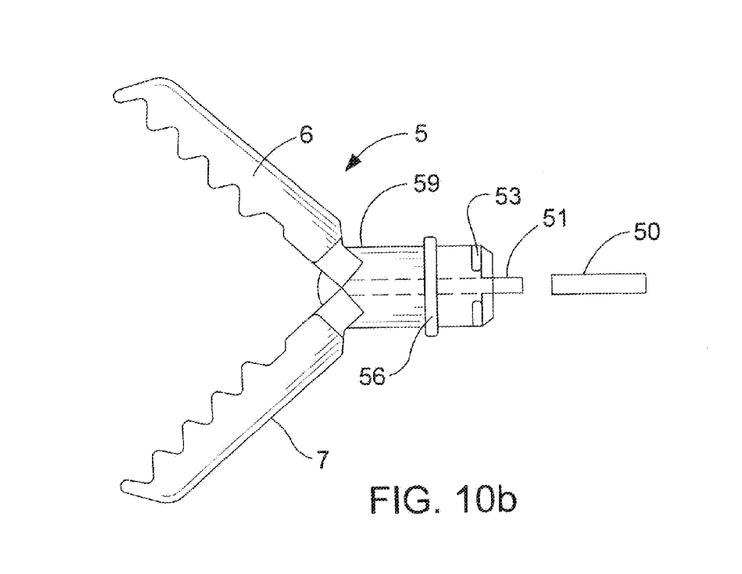
Figure 10C:
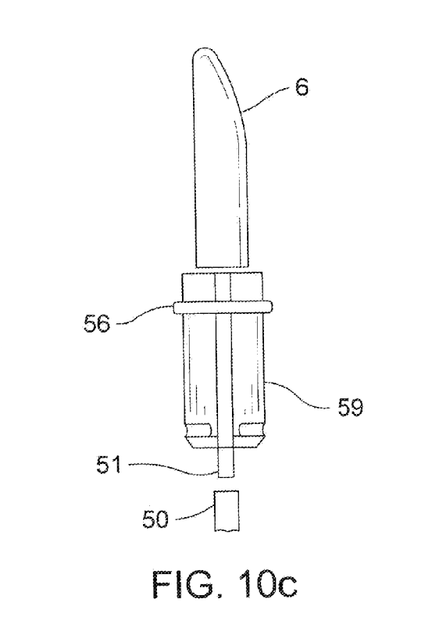

FIGS. 10*a* through 10*c* illustrate the basic workings of another embodiment of the inventive concept. FIG. 10*a* depicts an embodiment of the detachable head 5 of a separable grasping device with the upper and lower jaws 6, 7 in the closed position. Internal to the detachable head 5, and coaxially centered with the detachable head 5, is a driven shaft 51 of square cross-section which, when rotated clockwise along its axis, expands or contracts a tensionally-loaded locking ring 56. The locking ring 56, comprised of at least one winding, is affixed at one of its ends to a grasper head housing 59, and at its opposite end to the driven shaft 51. FIG. 10*a* shows the locking ring 56 having been expanded to near its limit, thereby causing the upper and lower jaws 6, 7 to close. FIG. 10*c* depicts the locking ring 56 having been tensionally released by reason of the driven shah 51 having been rotated in the counter-clockwise direction, thereby allowing the upper and lower jaws 6, 7 to open.

In FIG. 10*b*, the handle 2 of a separable grasping device is seen to comprise a longitudinal sleeve 52, which expands at its distal end into a circular u-joint 55. The u-joint 55 contains integral spring-loaded balls 54 symmetrically spaced around the inner perimeter of the u-joint 55. Contained within the sleeve 52 is a drive shaft 50, comprising a hollow, square cross-section which runs from the distal end of the sleeve 52 to its juncture, at the proximal end of the sleeve 52, with a control wheel 57. The hollow drive shaft 50 is of precise inner cross-sectional dimensions so as to allow a snug fit over the outer walls of the driven shaft 51. In this manner, when the detachable head 5 and the handle 2 are conjoined via the u-joint 55 and the groove 53 of the detachable head 5, the drive shaft 50, by means of the control wheel 57, can incrementally turn the driven shaft 51.

Also connected at the proximal end of the handle 2 is a gripping handle 58 which, by longitudinal connection means, operates to release the spring-loaded balls 53 from the circumferential groove 53, thereby disengaging the detachable head 5.

Variations of Equipment and Methods

By the nature of the surgical procedures presented herein, it is evident that other variations of the devices and the methods may be utilized, according to the medical requirements of a particular surgical procedure. As an alternative structure or embodiment of the disclosed device, a quadruple stem, or larger, puppet handle may also be utilized. As shown in the accompanying FIG. 8, the abdominally exiting needles, needle one 14 and needle two 15 may be stored in a similar compressible material 37 as shown in the triple puppet handle 21. To improve the versatility of operational use of the puppet handle, the stems may be joined at a common pivoting junction, serving to vary the relative angles between stems during surgery.

All embodiments of the puppet handles presented thus far may be constructed with a variety of means for retention of the abdominally exiting needles, 14, 15, said means including, but not limited to, latching, clamping, grasping, hooking, constricting, and clutching. In other words, the compressible material 37 is not the sole means of securely retaining the abdominally exiting needles 14, 15 in, or proximate to, the stem of a particular puppet handle.

It is recognized that one knowledgeable in the medical industry and skilled in the art, has the capability to design or produce similar, or other embodiments of this inventive concept. However all such variations, alterations, or modifications are entirely conceivable as being within the intent and scope of the present inventive concept. In particular, the essence of the inventive concept is the utilization of at least two surgical graspers comprising a detachable grasper head containing at least one length of suture, combined with the method of performing surgical manipulations with sutures attached to said grasper head and controlled exteriorly of the abdominal wall. Any number of connections, disconnecting methods, operational linkages, functions, and combinations thereof may be used to effectuate the engagement and disengagement of the detachable grasper head from its handle component.

What is claimed is:

1. A surgical apparatus for retracting, re-positioning, and re-orienting tissue or a bodily organ during endoscopic or laparoscopic procedures, comprising a) a detachable grasping head comprising an upper jaw and a lower jaw, said jaws being attached to a grasper head housing wherein a tensioned locking ring is attached to the perimeter of said grasper head housing, with a driven shaft attached to and concentric with the center of said grasper head housing; and b) a grasping handle having a proximal end and a distal end proximate said grasper head, and further comprising a hollow longitudinal sleeve, said longitudinal sleeve housing a drive shaft, which drive shaft connects, at the proximal end of the longitudinal sleeve, to a control wheel, and further, said drive shaft having at its distal end an expanded u-joint interiorly containing a plurality of spring-loaded balls, wherein said control wheel, when activated by a user, turns a driven shaft, said driven shaft being attached by a square fitting to said grasper shell; and c) a puppet handle comprising (i) a primarily cylindrical structure having a hollow left end and a hollow right end, wherein a compressible material is firmly compacted within the interior of said hollow left end and said hollow right end, said compressible material of such frictional coefficient as to enable the retention of at least one surgical needle inserted into said compressible material; and (ii) two exteriorly-attached, co-axial, flexible c-ring clips, each clip of an inner diameter corresponding to the outer diameter of said grasping handle.

2. A surgical apparatus according to claim 1, wherein said puppet handle further comprises:
the hollow left end and the hollow right end being conjoined, primarily cylindrical stems.

3. A surgical apparatus according to claim 1, wherein said puppet handle further comprises a pivoting common junction for at least two stems, each of said stems having a hollow opening wherein a compressible material is firmly compacted within the interior of said hollow openings, said material of such frictional coefficient as to enable the retention of a surgical needle inserted into said compressible material.

4. A method for the retracting, re-positioning, and re-orienting tissue or a bodily organ during endoscopic or laparoscopic surgery, comprising the steps of:
a) providing the surgical apparatus of claim 1 further comprising at least one needle retainer containing at least one surgical needle and suture and at least one suture harnessing means;
b) inserting a trocar, or other suitable medical instrument, having a first integral shaft and a second integral shaft, into the abdominal wall of a patient;
c) inserting, through said first integral shaft, said detachable grasping head and said grasping handle;
d) inserting, through said second integral shaft, an endoscope;
e) utilizing said endoscope, and clasping, by utilizing said detachable grasping head, tissue or an organ which is the subject of said surgery;
f) removing, by means of a device inserted through said second integral shaft, said needles from the at least one needle retainer;
g) passing each said needle through the interior of said abdominal wall so as to expose each said needle exteriorly to the patient's body;
h) affixing each of said needles and its accompanying suture separately into said compressible material within said hollow left end and said hollow right end, respectively, of said puppet handle; and
i) utilizing said puppet handle to retract and/or position said tissue or said organ to an orientation as required by the nature of said surgery.

* * * * *